United States Patent
Beck et al.

(10) Patent No.: US 6,916,010 B2
(45) Date of Patent: Jul. 12, 2005

(54) REGULATING VALVE FOR ADJUSTING THE FLOW IN AN INFUSION OR TRANSFUSION PROCEDURE

(75) Inventors: Bernd Beck, Rangendingen (DE); Jörg Weber, Edling (DE)

(73) Assignee: Smiths Medical Deutschland GmbH, Kirchseeon (DE)

(*) Notice: Subject to any disclaimer, the term of this patent is extended or adjusted under 35 U.S.C. 154(b) by 27 days.

(21) Appl. No.: 10/696,210

(22) Filed: Oct. 29, 2003

(65) Prior Publication Data

US 2004/0140444 A1 Jul. 22, 2004

(30) Foreign Application Priority Data

Oct. 29, 2002 (DE) ........................................ 102 50 391

(51) Int. Cl.⁷ ................................................ F16K 5/10
(52) U.S. Cl. ..................... 251/209; 251/286; 137/556.6
(58) Field of Search ................................ 251/209, 286, 251/288; 137/553, 556.6

(56) References Cited

U.S. PATENT DOCUMENTS

| | | | | |
|---|---|---|---|---|
| 4,750,707 A | * | 6/1988 | Johncox et al. | 251/304 |
| 5,005,604 A | * | 4/1991 | Aslanian | 137/556 |
| 6,726,175 B1 | * | 4/2004 | Saba et al. | 251/209 |

FOREIGN PATENT DOCUMENTS

| | | |
|---|---|---|
| DE | 83 12 029 U | 8/1983 |
| DE | 35 90 339 C2 | 3/1992 |
| DE | 42 01 416 A1 | 7/1993 |
| DE | 43 40 191 C1 | 2/1995 |
| JP | 2002035123 A | 2/2002 |

* cited by examiner

Primary Examiner—Edward K. Look
Assistant Examiner—John K. Fristoe, Jr.
(74) Attorney, Agent, or Firm—Dougherty, Clements, Hofer & Bernard

(57) ABSTRACT

The medical regulating valve for adjusting the flow in an infusion or transfusion procedure has a housing (2), and a valve chamber (21) into which an inlet connecting piece and an outlet connecting piece (22, 23) open. A rotating piece has a cylindrical valve plug (41) which can be inserted in the valve chamber (21) to form a seal between the plug and the chamber. The valve plug, has, on its outer periphery, at least one groove (42, 43) opposite the connecting pieces (22, 23) connecting the connecting pieces with one another in terms of flow and having a cross-section changing in the peripheral direction. An insert (3) having the shape of an annular disc overlaps the valve chamber (21) and has, on its side facing the rotating piece (4), a number of markings (35, 36, 37) lying on concentric circles. Provided on the rotating piece (4) are a number of windows (45, 46, 47) which are offset with respect to each other in the peripheral and radial directions, each being opposite one of the markings (35, 36, 37).

23 Claims, 12 Drawing Sheets

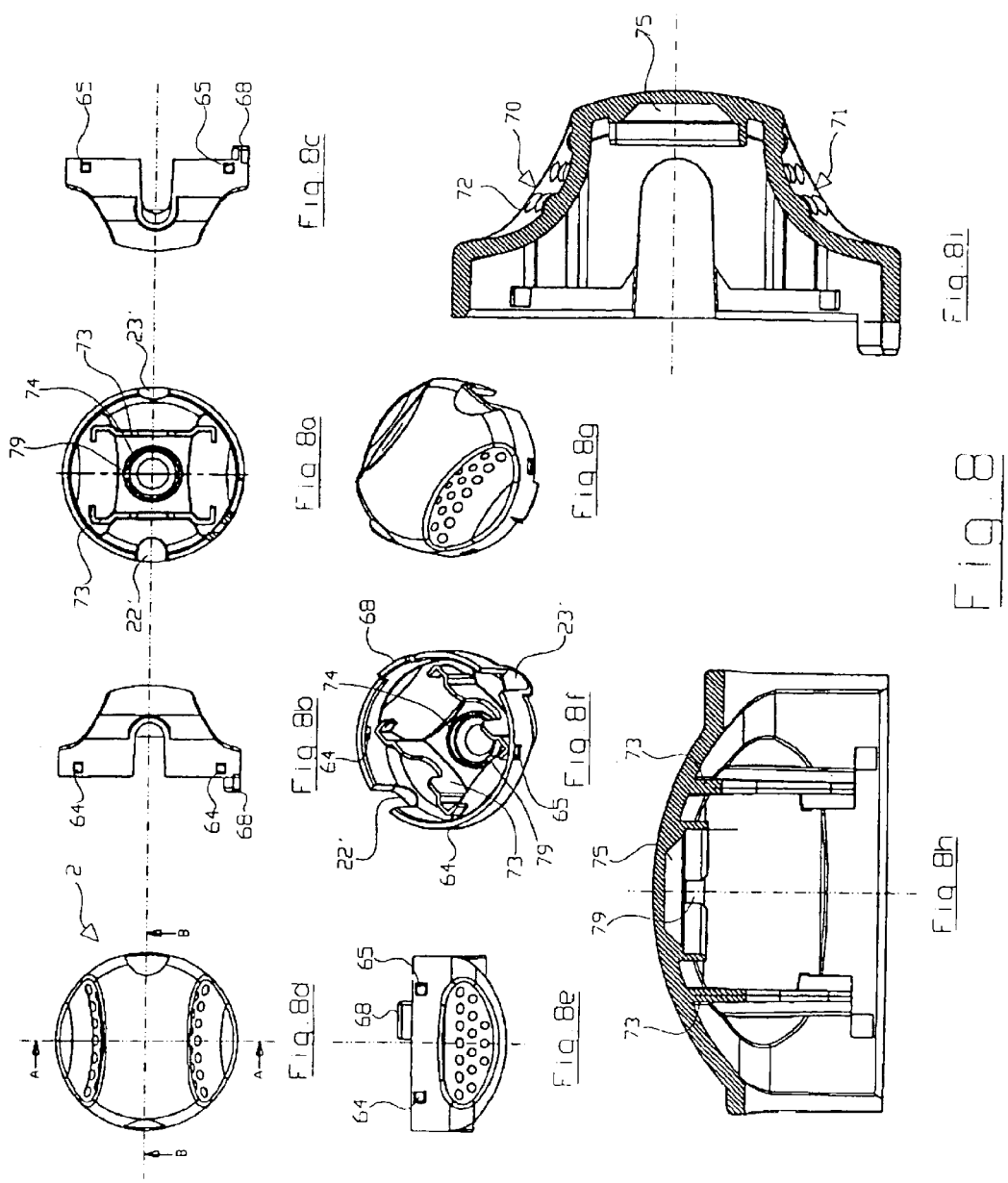

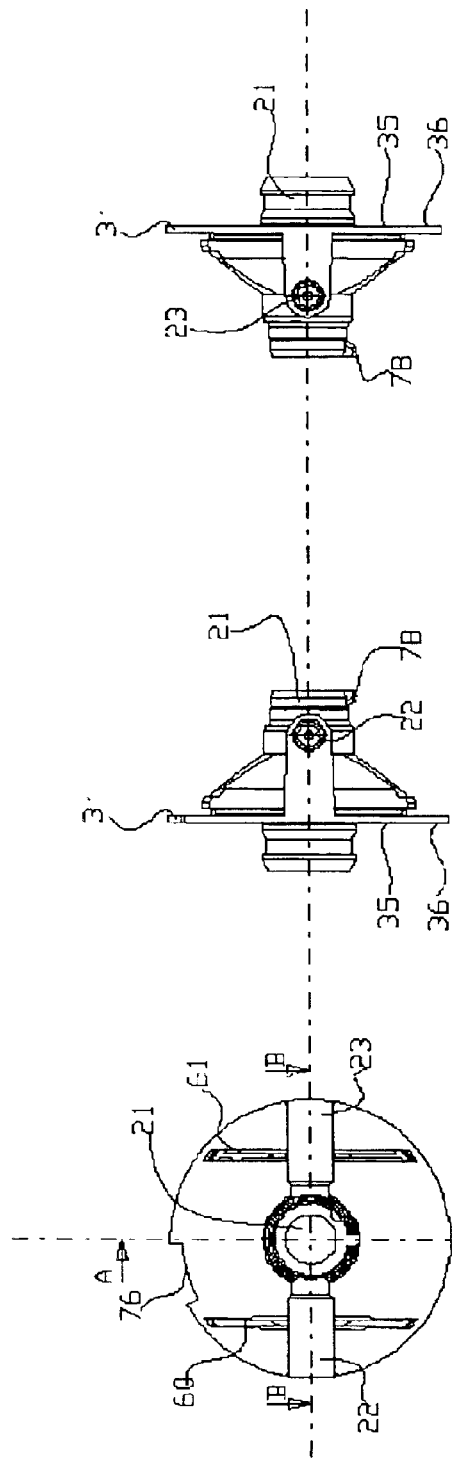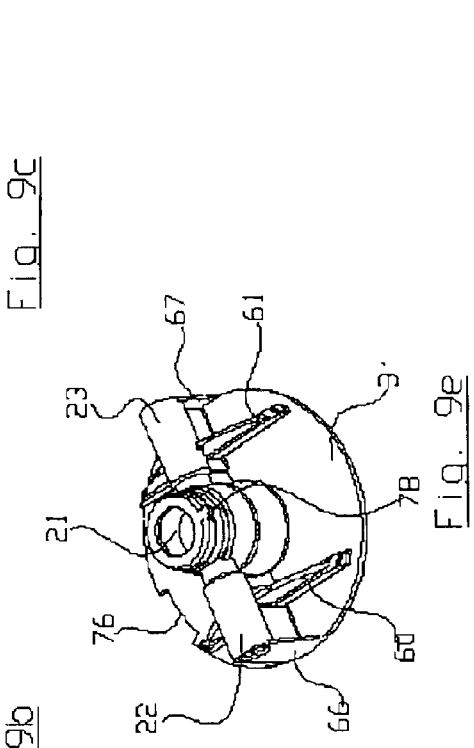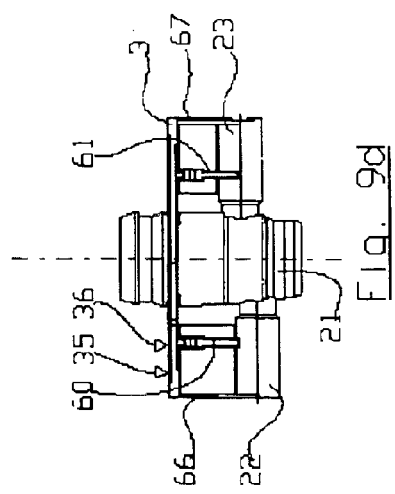

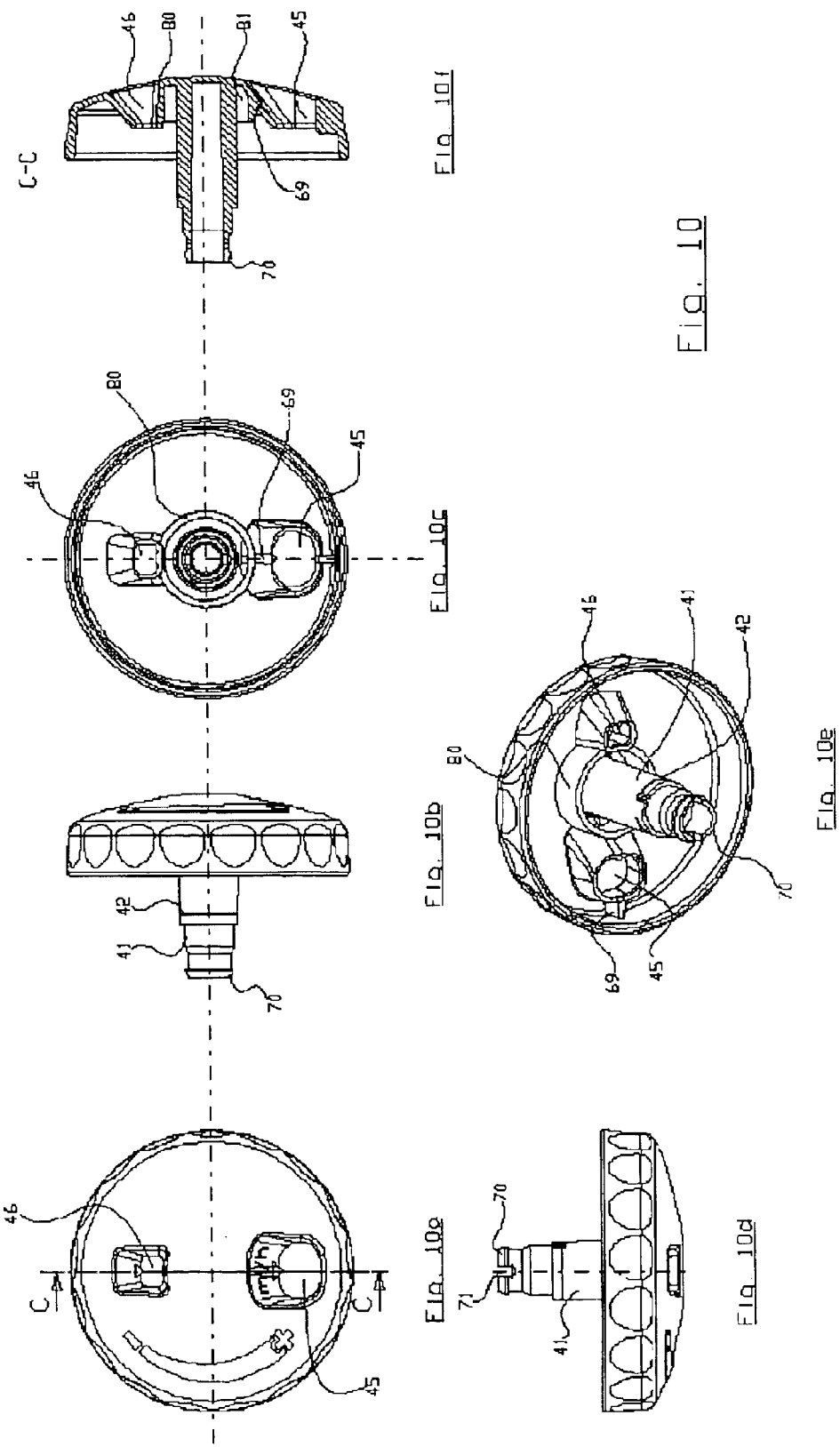

US 6,916,010 B2

REGULATING VALVE FOR ADJUSTING THE FLOW IN AN INFUSION OR TRANSFUSION PROCEDURE

BACKGROUND

1. Field of the Invention

The invention relates to a regulating valve for adjusting the flow in an infusion or transfusion procedure, and more particularly to a regulating valve having selectable known flow rates.

2. Prior Art

A valve of this kind is known from DE 83 12 029 U. This regulating valve has a cup-shaped housing with an inlet connecting piece and an outlet connecting piece, which open into a hollow cylindrical valve chamber, and a rotating piece with a cup-shaped foundation and, at a distance therefrom, a cylindrical valve plug which can be inserted into the valve chamber to form a seal at the outside and has, on its outer periphery, at least one groove opposite the connecting piece which connects the connecting pieces in terms of flow and which has a cross-section changing in the peripheral direction.

A similar regulating valve is described in DE 43 40 191 C1. In order to limit the rotation of the rotating element here, complementary stops are provided on the base of the cup-shaped housing and on the base of the cup-shaped rotating element.

DE 42 01 416 A1 has a rotating element with two annular grooves offset from each other in the axial direction and connected with each other by means of a channel running axially. Therefore, the inlet connecting piece and the outlet connecting piece can be offset from one another in the axial direction.

A further similar regulating valve is described in DE 35 90 339 C2. Here, the face of a cylindrical rotating element has a groove which widens in the peripheral direction and inlet and outlet connecting pieces opening into the base of a cup-shaped housing. The condition for satisfactory functioning here is a sealing contact between the base of the housing and the face of the rotating element because it would be possible otherwise for a flow connection between the inlet and outlet connecting pieces outside the groove.

JP 2002035123 A shows a calculating disc for calculating the flow rate in a drip infusion. A number of scales are located on concentric circles on a flat plate. A rotating disc above the latter has a number of windows which are shaped like segments of a circle and through which the scales can be viewed.

The flow rate in such regulating valves depends not only on the effective cross-section, but also on the hydrostatic pressure. The container with the infusion fluid is usually fastened to an infusion stand, the container being mounted on the stand at a prescribed height. One customary height is, for example, 50 cm above the infusion point on the patient. A change in this height also leads to a change in the drip rate.

It would be desirable for hospital personnel if they could obtain information about the drip rate as a function of the hydrostatic pressure and as a function of the rotational position of the rotating element in a way that the effect of a change in the hydrostatic pressure, that is, the height of the container, can be estimated even before there is a change in the height. In addition, the regulating valve should be simple with respect to structure and mounting, simple meaning operable with one hand and making it possible to have a precise adjustment of the flow rate. Furthermore, with the present flow regulating valves, a common limitation is that the flow rates are accurate for low viscosity fluids, such as saline solutions. Saline (isotonic salt) solutions, typically with low viscosities, are nominally used to calibrate regulating valves, and thusly commonly do not have good correlation with fluids of higher viscosity. When regulating fluids having higher viscosity, the usual scales are not applicable, and in fact may be misleading to the point of having serious negative consequences. Therefore, it would be advantageous for the user to have a scale or markings showing the flow rates for fluids having a higher viscosity. Accordingly, what is needed is an invention comprising a first standard scale for isotonic salt solutions, wherein said invention can be cross-referenced to indicia of fluids having a higher viscosity. The cross-reference can refer to empirical results in a manual or digital library or to a mathematical algorithm.

OBJECTS OF THE INVENTION

A principal object of the invention is a regulating valve for adjusting the flow in an infusion or transfusion procedure, wherein the valve has a relatively few number of components and therefore is less subject to failure of.

Another object of the invention is a valve, wherein many of the functional features of the components are integral to one of the components, so that the valve is relatively easy to manufacture as there are relatively few components.

A further object of the invention is a valve that is easy to read, and provides the user tactile feedback as well as visual feedback that the valve is set at the desired flow rate. Other advantageous features of the invention will become apparent from the description and the appended claims.

SUMMARY OF THE INVENTION

The operational features of the invention are largely provided by the basic principles incorporated in the provision of a rotating element cover having a number of openings or windows. The openings or windows are distributed around the periphery of the rotating element cover. The openings or windows are positioned so as to be in an offset arrangement with respect to each other. The valve has a housing, and inside the housing and below the windows of the rotating element cover, there are a number of markings or scales that correspond to a specific window. From the markings and the window it can readily be seen what is the flow rate.

BRIEF DESCRIPTION OF THE DRAWINGS

The invention is explained in more detail below using an example embodiment in connection with the drawing in which:

FIG. 8 shows different representations and views of the housing of the example embodiment in FIG. 7.

FIG. 10 shows different representations and views of the rotating piece of the example embodiment in FIG. 7.

DETAILED DESCRIPTION

Figure 1:
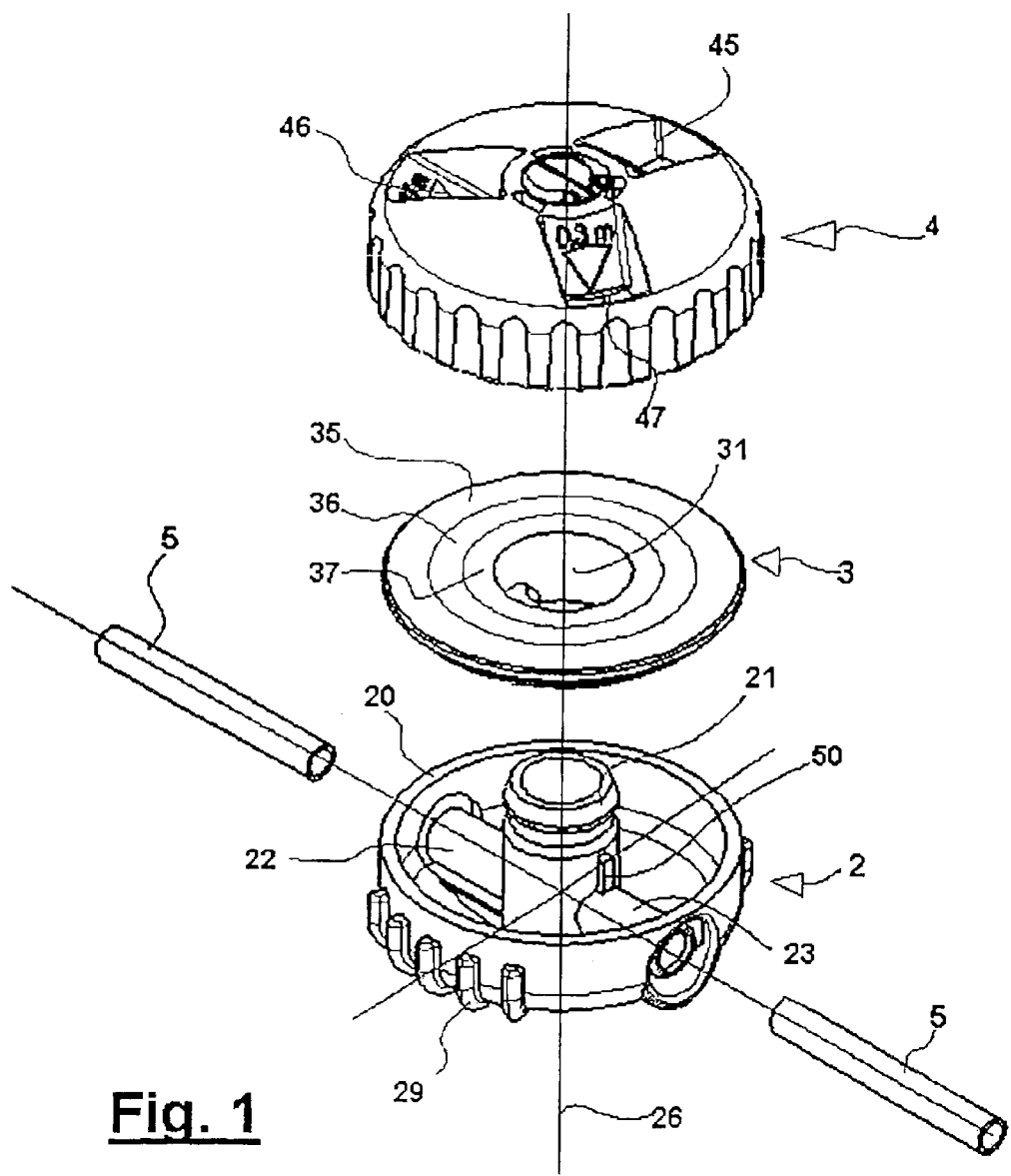
FIG. 1 shows an exploded view of the invented regulating valve.

Reference is made first to FIG. 1. The regulating valve, designated as a whole with reference symbol 1, has a housing 2, an insert 3 and a rotating piece 4. The regulating valve is connected by two tube ends 5 with a container for the infusion fluid and a blood vessel of the patient (not shown).

The housing 2 has a cup-shaped foundation 20 with an integrally cast hollow cylindrical and stack-like valve chamber 21, and two side connecting pieces 22 and 23 for the tubes (5 in FIG. 1) which are connected through openings 24 and 25 with the interior of the cylindrical valve chamber 21. The two connecting pieces 22 and 23 are, relative to the longitudinal axis, in an offset arrangement with respect to each other (cf. FIG. 2d) and are opposite each other by 180 degrees in the peripheral direction. Integrally cast on the outer periphery of the cup-shaped foundation 20 are a number of gripping nubs 29 which permit a firm hand-hold which is resistant to twisting.

Also provided is an insert 3 that is substantially an annular disc with a central opening 31 that overlaps the valve chamber 21. That is, the insert 3 is pushed over the valve chamber 21. Markings 35, 36 and 37 are applied to a number of concentric circular paths on the insert 3 at its top side facing away from the housing. The insert 3 is clearly localized with respect to the housing 2, as will be seen later herein.

Finally, the regulating valve has a rotating piece 4, which has, as will be explained in more detail in connection with FIG. 4, a cup-shaped housing and a hollow cylindrical valve plug at a distance therefrom which engages the valve chamber 21. The outside of the rotating piece has a number of windows 45, 46 and 47 which are uniformly distributed in the peripheral direction, and which are in an offset arrangement with respect to each other in the radial direction. Each window 45, 46 and 47 correlates to the concentric circular paths having markings 35, 36, 37, and the corresponding marking can be read through the assigned window.

The regulating valve thus consists in principle of only three parts which, for example, are made of plastic using the injection molding process. The three parts are very easy to assemble. The insert is simply mounted and the rotating piece 4 is then slipped over it and locked thereon by a spring lock which is described later.

Figure 2:
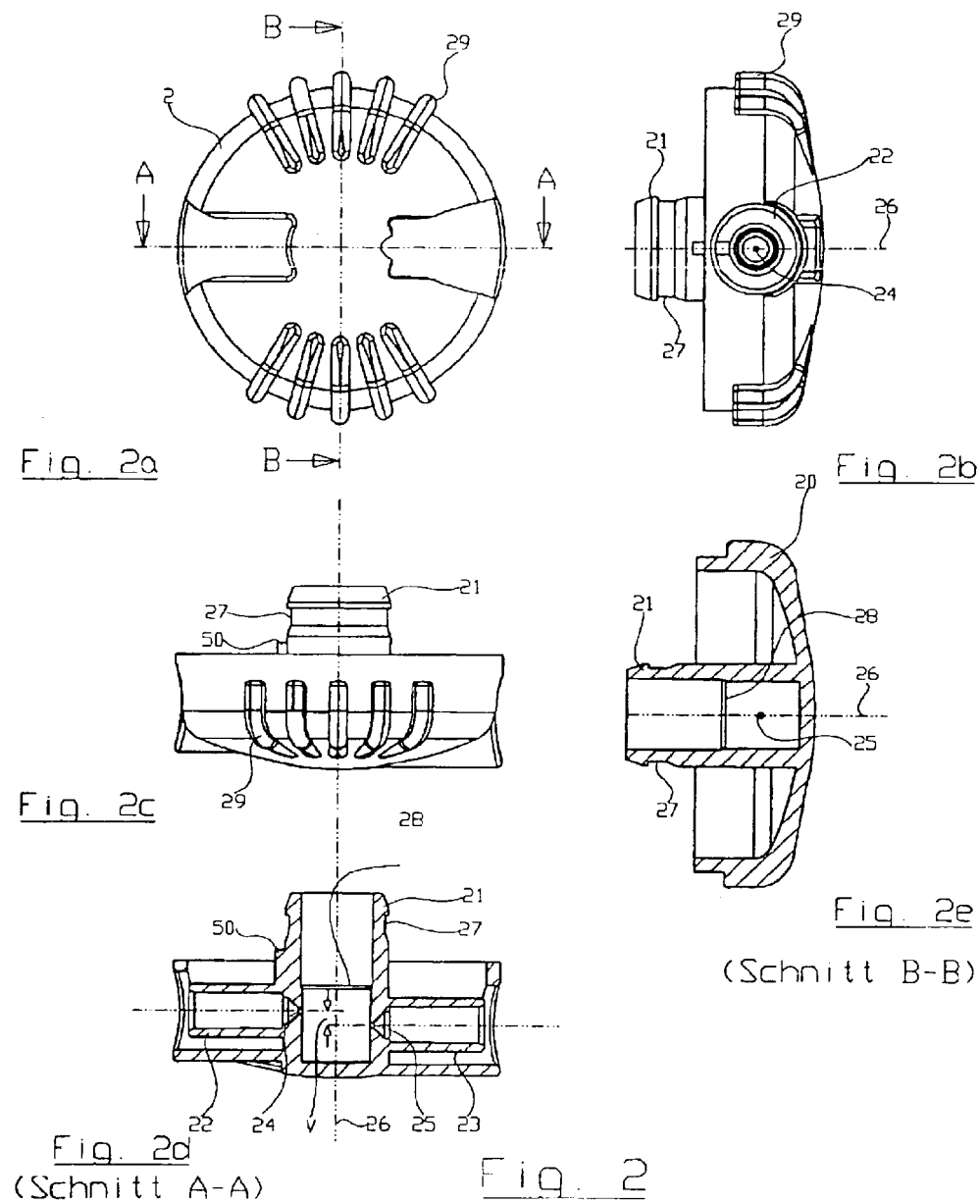
FIG. 2 shows a view from the bottom of the housing of the regulating valve (FIG. 2a), two side views (FIGS. 2b and 2c) and two sectional views (FIGS. 2d and 2e)

FIG. 2 shows different views of the housing 2. It has a cup-shaped foundation 20, the hollow cylindrical valve chamber 21 being at the middle at a distance therefrom. Integrally cast on the outside of the valve chamber are the two connecting pieces 22 and 23 which are in a flow connection with the interior of the valve chamber 21 through openings 24 and 25. The two connecting pieces 22 and 23 are, relative to the axis of rotation 26 of the regulating valve, offset from one another by a distance V. Provided at the outside of the free end of the valve chamber is a catch indentation 27 which is engaged by a detent of the rotating piece. A radial projection serving as a rotation limiting stop 50 is provided in the transition area between the one connecting piece 22 and the valve chamber 21 on the periphery of the valve chamber 21.

Seen in the sectional views of FIGS. 2b and 2d is an edge 28 from which the valve plug (FIG. 4) is in a radially sealing engagement.

Figure 3:
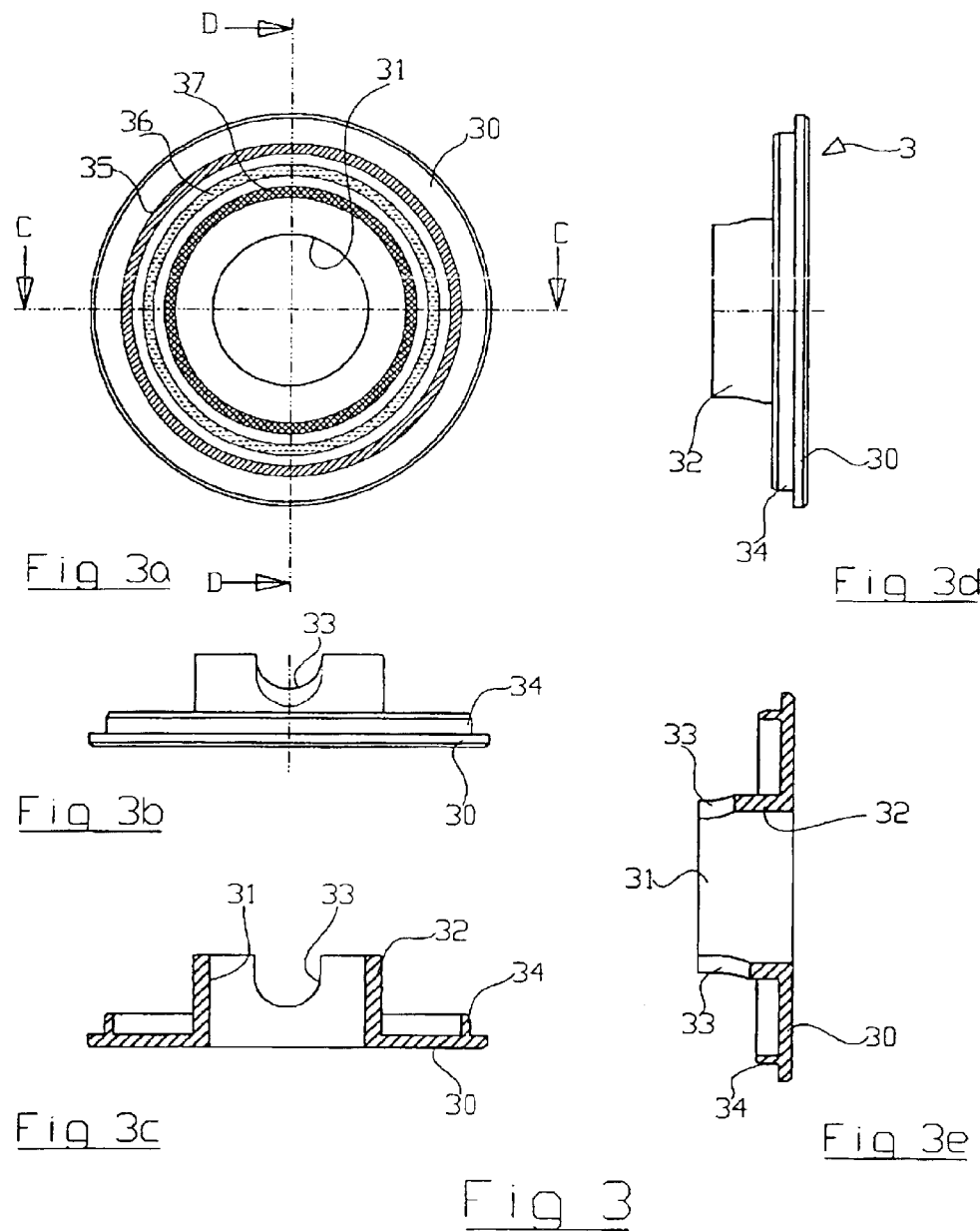
FIG. 3 shows different views of an insert element: a top view (FIG. 3a), two side views (FIGS. 3b and 3d) and two sectional views (FIGS. 3c and 3e)

FIG. 3 shows the insert 3 which forms a flat annular disc 30 with an opening 31 around which there is a cylindrical projection 32 at a distance. The free end of the projection 32 has two recesses 33 with semicircular base facing each other which overlap the peripheries of the connecting pieces 22 and 23 (from FIG. 2). This maintains a twist-free hold on the insert 3 in the housing 2. The annular disc 30 also has, close to the outer periphery, a centering spigot for centering with respect to the housing 2. This centering spigot is at a distance from the annular disc 30 in the same direction as the projection 32.

On the upper side of the annular disc 30 in FIG. 3a, the user can see markings or scales 35, 36 and 37 applied to concentric rings. They are, for example, in the form of numerical values for drip rates as a function of the position of the rotating piece (4 in FIG. 1), the numerical values in a radially offset arrangement with respect to each other indicating different hydrostatic pressures or heights of the containers with the infusion fluid.

It can be seen in FIGS. 3b, 3c and 3e that the recesses 33 facing each other have different depths, that is, in accordance with the axial displacement of the connecting pieces 22 and 23 (FIG. 2).

Figure 4:
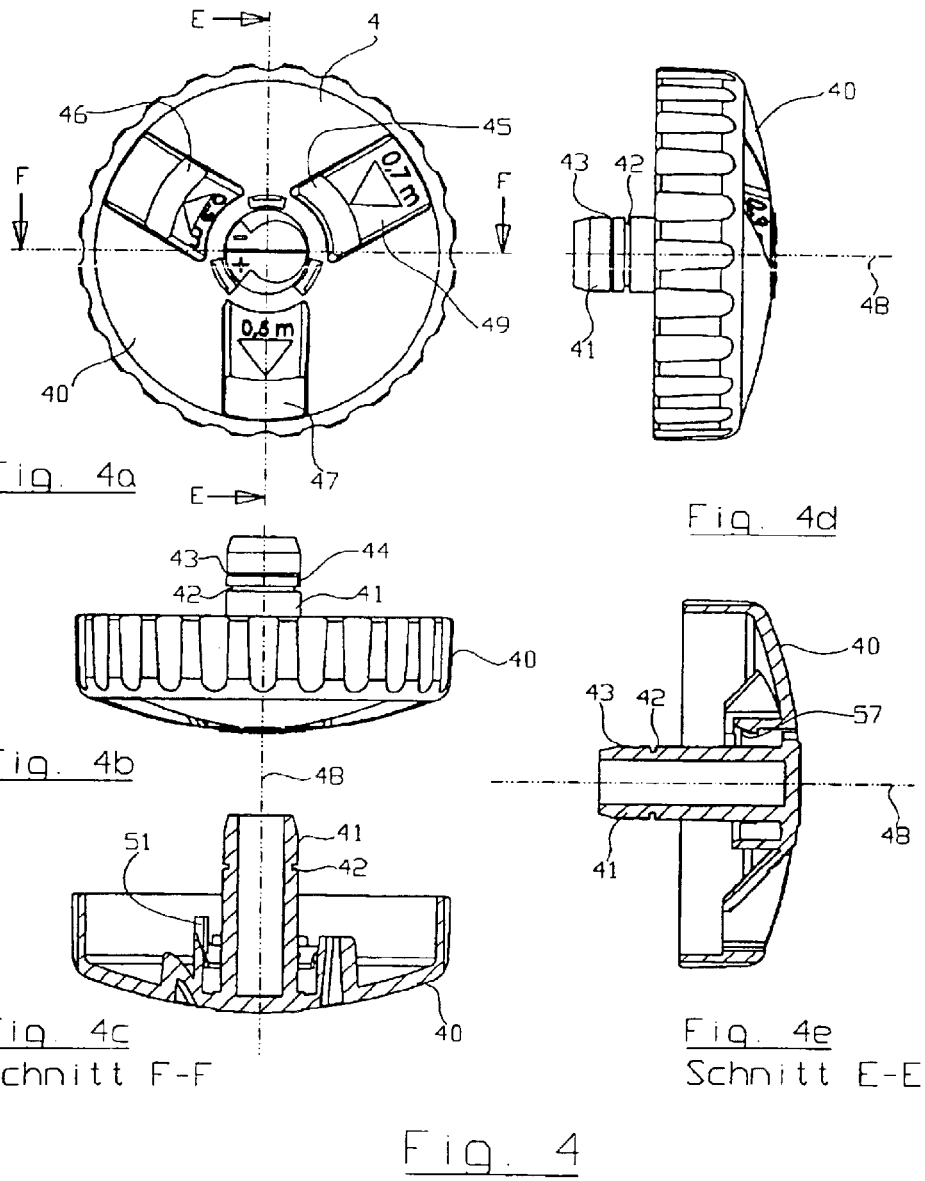
FIG. 4 shows different views of the rotating element, that is, a top view (FIG. 4a), two side views (FIGS. 4b and 4d) and two sectional views (FIGS. 4c and 4e)

FIG. 4 shows the rotating piece 4 which also has a cup-shaped foundation and a hollow cylindrical valve plug 41 at a distance therefrom. The outer periphery of the valve plug 41 has two annular grooves 42 and 43 which are offset from one another in the axial direction. The one groove 42 has a constant depth and a constant cross-section, while the other groove 43 has, in the peripheral direction, a steadily changing cross-section, that is a steadily changing depth and, in the peripheral direction, covers a limited range which is 330 degrees here, for example. Provided at the start of the groove 43 where the depth is greatest is an axial channel which connects the two grooves 42 and 43 with one another.

As can be best seen in FIG. 4a, the foundation 40 has a number of windows 45, 46 and 47 which are offset 120 degrees from each other in the peripheral direction and are also in a radially offset arrangement with respect to the axis of rotation 26 so that they do not overlap each other. Provided next to the windows 45, 46 and 47 are recesses 49 in which there is a marking, for example, a printing which indicates the different heights such as 0.5 m, 0.3 m and 0.7 m. Also viewable is a reading arrow pointing to the marking of the underlying marking of the annular disc 30.

As can be best seen in FIG. 4e, the foundation 40 has, concentric to the valve plug 41, a projection with a catch hook which cooperates with the catch recess 27 of the housing (FIG. 2) and forms a rigid connection of the rotating piece with the housing following assembly.

In order to limit rotation, there are two stops, a rotation limiting stop 50 on the housing 2 above the connecting piece 22 of the valve chamber 21, and an interacting rotation stop 51 on the rotating piece 4. The rotation limiting stops 51 and 50 are arranged and dimensioned in the peripheral direction so that it is possible to run through the full effective range of the groove 43, e.g., a range of 330 degrees in this case.

Figure 5:
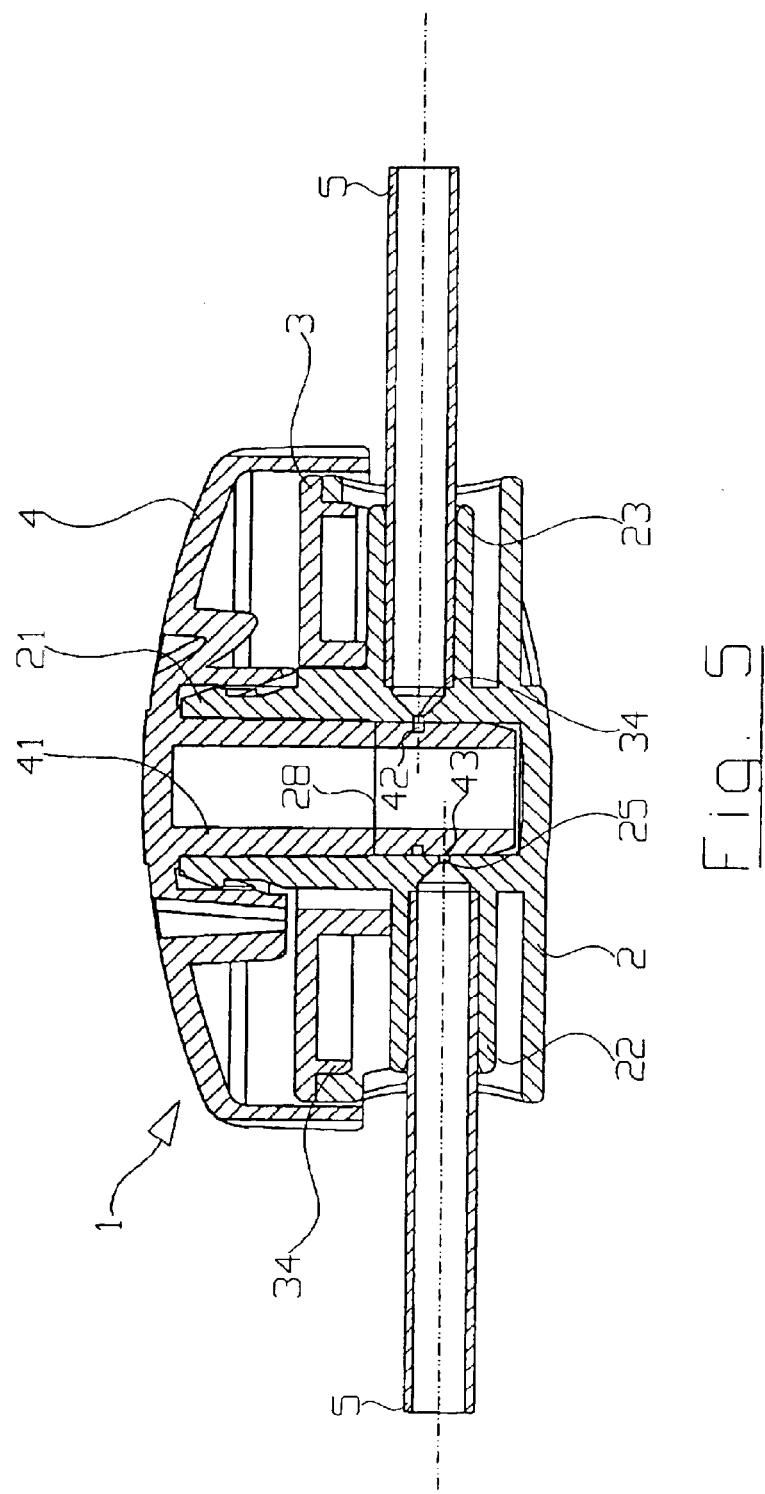
FIG. 5 shows a cross-section of the assembled regulating valve.

FIG. 5 shows a cross-section through the assembled regulating valve. Assembly is as follows. The insert 3 with its projection 32 is first pushed over the valve chamber 21 of the housing and oriented in the rotating direction of the insert 3 so that the recesses 33 reach over the connecting pieces 22 and 23. Because of the different axial height of the connecting pieces 22 and 23 and the corresponding different depth of the recesses 33, a specific position in the direction of rotation is set. Furthermore, the centering collar 34 engages the edge of the housing 2, which means that the insert 3 will assume a specific position.

The rotating piece 4 is then inserted, its valve plug 41 engaging the opening of the valve chamber 21 of the housing 2. The mutual engagement of the catch recess 27 and the detent 57 of the rotating piece results in an axial locking. The groove 42 on the valve plug 41 of the rotating piece 4 is then correctly positioned with respect to the opening 24 so that the tube 5 of the connecting piece 23 is in a flow connection with the groove 42. The groove 42 is connected through the channel 44 with the spiral groove 43, which creates a flow connection of the opening 24 with the opening 25. The effective cross-section of said flow connection thereby depending on the position of the rotating piece 4.

The edge 28 defines the zone between the valve chamber 21 and the valve plug 41 from which point the two parts lie against one another to form a seal. The part of the valve plug 41 starting at the edge 28, which also bears the two grooves 42 and 43 is made of a material having a hardness which is different from that of the valve chamber 21 so that a good sealing engagement is created there. The seal is effective only in the surface area of the valve plug 41. The face of the valve plug 41 is at a distance from the base of the recess of the valve chamber 21, so that the catch connection 27 between 57 is determines the axial centering of the housing and rotating piece. A slight axial play does not have any influence on the seal, but it probably can influence the orientation between openings 24 and 25 relative to grooves 42 and 43. If openings 24 and 25 are made somewhat wider than the width of grooves 42 and 43, however, no change in the flow rate will occur, even with an axial play.

Figure 6:
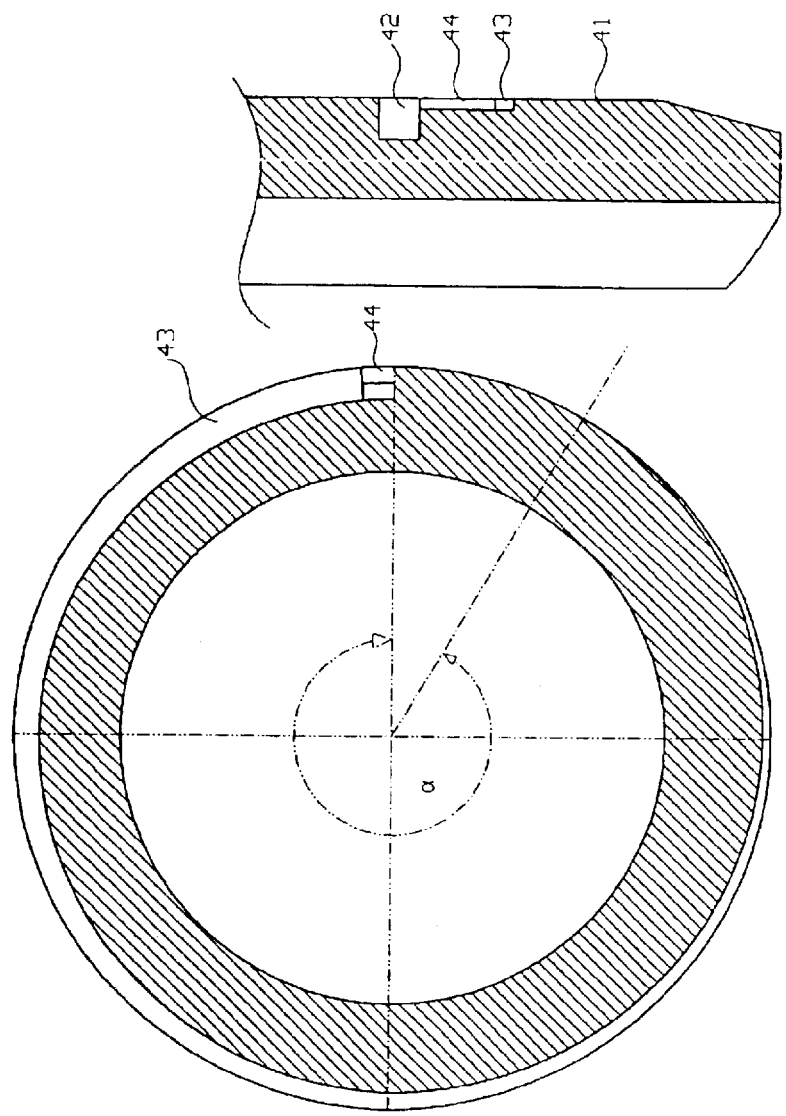
FIG. 6 shows two sections through the rotating element in the area of the annular groove as a cross-section (FIG. 6a) and as a longitudinal section (FIG. 6b).

Referring again to FIG. 6, the Fig. shows the grooves 42 and 43 as well as the channel 44 in more detail. The groove 42 is an annular groove with a constant cross-section, while the groove 43 is a spiral groove running in the peripheral direction indicated by angle α. The angle α controls the depth, which decreases to a value of zero. The beginning of the groove 43 is continuously and fully supplied with fluid from the channel 42. Depending on the position of the rotating piece 4, a different depth of the groove 43 lies opposite the opening 25 and thus determines the flow rate.

It can be seen from the description above that the assembly is very simple and can be done with a few manipulations. Later operation of the regulating valve is also very simple and with a little skill can also be carried out with one hand. The flow rate for different heights of the container with the infusion fluid can be conveniently read through the windows 45, 46 and 47.

Figure 7:
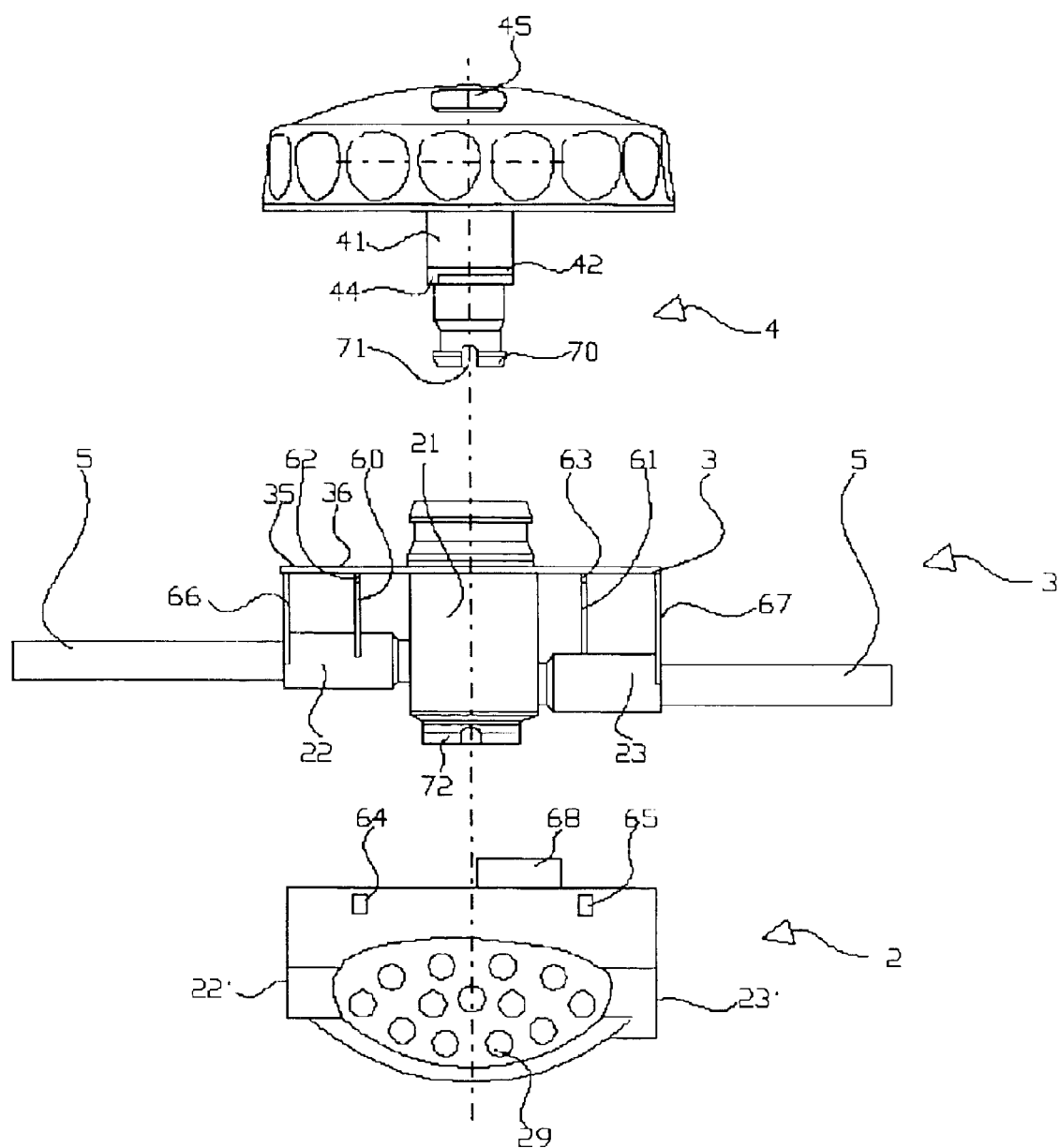
FIG. 7 shows an exploded view of a regulating valve in accordance with a second example embodiment of the invention.

The example embodiment in FIGS. 7 to 11 is basically differentiated from that in FIGS. 1 to 6 by the following modifications, reference being made first to FIG. 7. The insert element 3 inserted into the housing 2 contains, in the case of the example embodiment in FIG. 7, the valve chamber 21, the two connecting pieces 22 and 23 and the annular disc, which is designated here with the reference symbol 3'. This complete insert 3 is then inserted into the housing 2. The annular disc with the imprinted scales is thus connected to the valve body and the housing 3 was separated from the valve body. The housing 2 is thus a separate injection molded part with gripping surfaces 29 which is connected with the insert 3 through a snap connection. Furthermore, the rotating stop for the rotating piece was placed on the outer edge of the housing in this example embodiment.

The positive connection (catching or snapping into place) is carried out on the one hand between the rotating piece and the valve body and on the other hand between the housing and the valve body.

Finally, this example embodiment provides only two viewing windows for reading the scales.

To the extent FIGS. 7 to 11 have the same reference symbols in the example embodiment as in FIGS. 1 to 6, corresponding parts are the same in terms of designation or function.

Reference is now made in detail to FIG. 7. The housing 2 has a cup-shaped foundation with two side recesses 22' and 23' for accommodating the connecting pieces 22 and 23 of the valve body 3 which is inserted into the housing from above. At a distance from connecting pieces 22 and 23 are disc-shaped webs 60 and 61, each with two detents 62, 63 which can engage detent openings 64, 65 of the housing 2 and thus firmly anchor the valve body 3 in the housing 2. Fastened on the webs 60 and 61 is the annular disc 3' overlapping the valve chamber 21 and bearing the scales to be read. In addition, this disc can be also fastened to the connecting pieces by means of further webs 66 and 67.

Provided on the upper edge of the housing 2 is an axially projecting rotating stop 68 which cooperates with a counter-stop 69 (FIG. 10) of the rotating piece.

Mounted on the free end of the valve plug 41 is a rotating detent 70 which has elastic properties due to axial slots 71 and, when the valve plug is introduced into the valve chamber 21, projects out of the open bottom side 72 thereof and locks into place behind the face located there.

FIG. 8 shows the housing 2 in a plan view from above (FIG. 8a), side views from right and left (FIGS. 8b and 8c), a view from below (FIG. 8d), an elevation (FIG. 8e), a perspective plan view (FIG. 8f), a perspective view from below (FIG. 8g) as well as a sectional view along the line B—B (FIG. 8h) and along the line A—A (FIG. 8i). Provided on the bottom side of the housing are indentations 70 and 71 with gripping nubs 72 by means of which the housing can be gripped well with one hand without slipping. Provided inside the housing are webs 73 and 74, webs 73 being adapted to the shape of the connecting pieces 22 and 23 as well as that of the webs 62, 63, 66 and 67, so that the insert part 3 is maintained there positively. The web 74 in the housing is annular and serves for centering of the valve chamber 21. A further recess 75 in the base of the housing serves for receiving the free end of the valve plug 41 projecting out of the valve chamber 21.

Figure 9G:
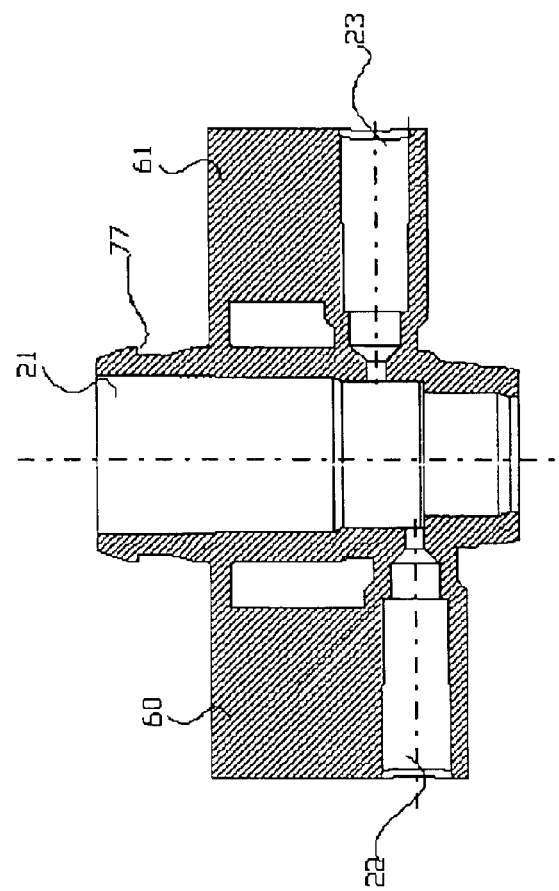
FIG. 9 shows different representations and views of the valve body of the example embodiment in FIG. 7.
Figure 9F:
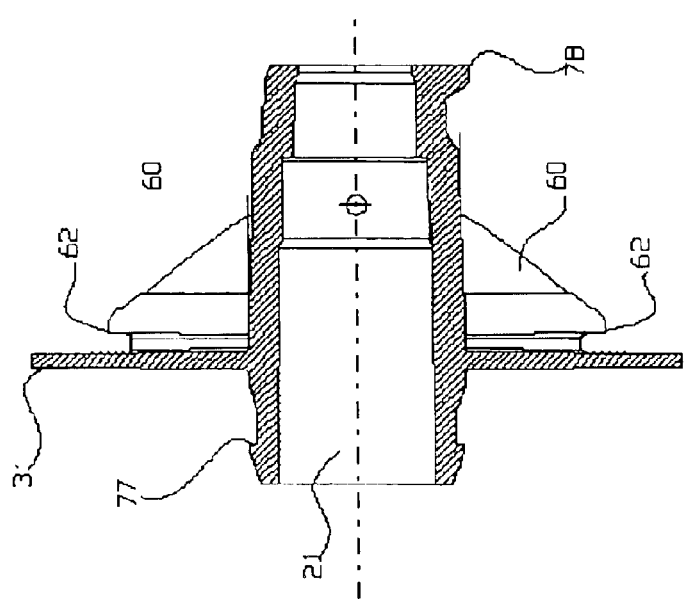

FIG. 9 shows the valve body 3 in a underside view (FIG. 9a), side views from left and right (FIGS. 9b and 9c), an elevation (FIG. 9d), a perspective view angled from the underside (FIG. 9e) as well as sectional views along the line A—A of FIG. 9a (FIG. 9f) and along the line B—B (FIG. 9g).

These figures are understandable per se with the reference symbols indicated in connection with the description above of FIG. 7. It can also be seen from FIGS. 9a and 9b that the outer periphery of annular disc 3' has a recess 76 for passage of the stop 68 of the housing 2 (cf. FIG. 7). It can be seen moreover that there is a projection 77 rotating on the upper outer edge of the valve body and engaging a recess 81 of the rotating piece described later. Provided on the bottom end of the valve body 21 is a projection 78 (cf. FIGS. 9b, 9e and 9f) which engages a recess 79 (cf. FIG. 8h) in the web 74 of the housing for additional orientation of the valve body relative to the housing. The projection 78 is preferably also the injection point during injection molding production of the part.

FIG. 10 shows the rotating piece 4 in a plan view from above (FIG. 10a), a side view (FIG. 10b), a view from below (FIG. 10c), an elevation (FIG. 10d), a perspective view slanting from below (FIG. 10e) and a sectional view along the line C—C of FIG. 10a (FIG. 10f). The rotating piece is cup-shaped here too and has windows 45, 46 for reading the scales on the annular disc 3'. Seen in FIG. 10f and 10e is the stop 69 which serves as counter-stop to the stop 68 of the housing 2 (FIG. 7) and limits the rotation of the rotating piece.

Also seen on the free end of the valve plug 41 is the detent 70 which locks the rotating piece on the valve body 3. Seen going around the valve plug 41 is an axially projecting edge 80 which runs at a radial distance from the valve plug 41, so that an annular space 81 is formed which is engaged by one end of the valve chamber with the projection 77 so that the rotating piece is guided or supported relative to the valve body 3.

Figure 11F:
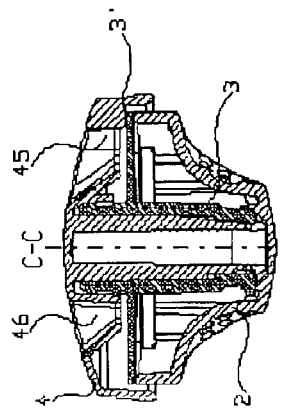
FIG. 11 shows different representations and views of the assembled regulating valve of the example embodiment in FIG. 7.
Figure 11C:
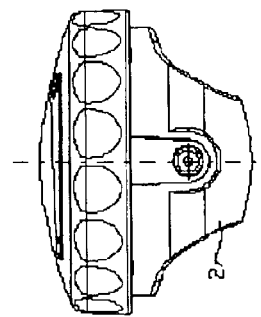
Figure 11D:
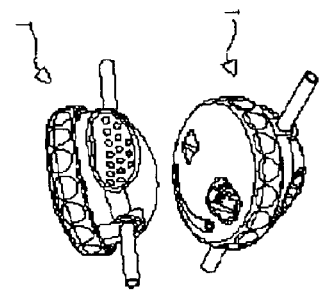
Figure 11A:
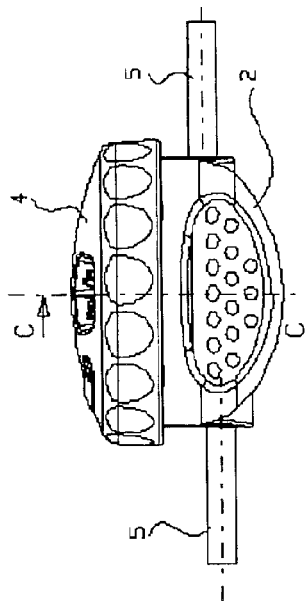
Figure 11B:
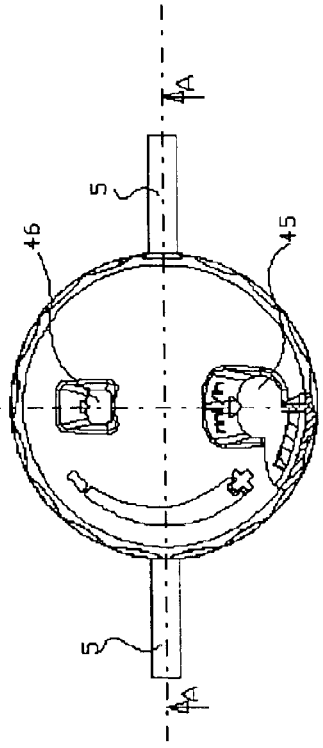

FIG. 11 shows the regulating valve in the assembled condition in a side view (FIG. 11a), plan view (FIG. 11b), in a side view turned 90 degrees (FIG. 11c), in two perspective views at a slant from the top and from the bottom (FIG. 11d) as well as a sectional view along the line A—A of FIG. 11b (FIG. 11e) and a sectional view along the line C—C of FIG. 11a (FIG. 11f).

Figure 11E:
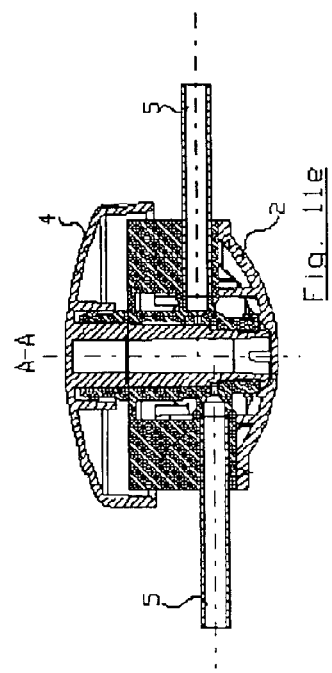

The sectional drawings of FIGS. 11e and 11f clearly show the assembled condition and how the individual components engage one another or are adjusted to one another. Because of the detailed individual drawings and the associated description, no further explanations are needed since a person skilled in the art will readily recognize the structure and assembly as well as the function.

It is to be understood that the foregoing description and specific embodiments are merely illustrative of the best mode of the invention and the principles thereof, and that various modifications and additions may be made to the apparatus by those skilled in the art, without departing from the spirit and scope of this invention, which is therefore understood to be limited only by the scope of the appended claims.

What is claimed is:

1. A regulating valve for adjusting the flow in an infusion or transfusion procedure, said regulating valve comprising: a housing; connecting pieces essentially consisting of an inlet connecting piece and an outlet connecting piece opening into a hollow cylindrical valve chamber; a rotating piece that has a cup-shaped foundation and a cylindrical valve plug extending therefrom, wherein said cylindrical valve plug is inserted into the valve chamber sealing the radial outside periphery of the valve plug and the radial inside periphery of the valve chamber; where said rotating piece has, on a periphery, at least one groove that is opposite the connecting pieces and which constrictingly connects the connecting pieces in terms of flow, where said rotating piece has a changing cross-section in the peripheral direction, characterized by an annular disc which overlaps the valve chamber and has, on a side facing the rotating piece, a number of markings lying on concentric circles; and wherein the rotating piece has a number of windows that are in an offset arrangement with respect to each other in the peripheral and radial directions, where each window is lying opposite a marking.

2. The regulating valve as described in claim 1, characterized in that the annular disk has, at an axial distance, an annular centering collar which engages the housing.

3. The regulating valve as described in claim 2, characterized in that the annular disk has a cylindrical projection which has, on its face, opposing recesses which overlap the connecting pieces of the housing.

4. The regulating valve as described in claim 3, characterized by the provision on the outside of the valve chamber of a rotation limiting stop cooperating with a rotation limiting stop on the rotating piece.

5. The regulating valve as described in claim 4, characterized in that the valve chamber has, on its outside, a catch recess and in that the rotating piece has, concentric to the valve plug a cylindrical projection with at least one detent which engages the catch recess.

6. The regulating valve as described in claim 3, characterized in that the valve chamber has, on its outside, a catch recess and in that the rotating piece has, concentric to the valve plug a cylindrical projection with at least one detent which engages the catch recess.

7. The regulating valve as described in claim 2, characterized by the provision on the outside of the valve chamber of a rotation limiting stop cooperating with a rotation limiting stop on the rotating piece.

8. The regulating valve as described in claim 7, characterized in that the valve chamber has, on its outside, a catch recess and in that the rotating piece has, concentric to the valve plug a cylindrical projection with at least one detent which engages the catch recess.

9. The regulating valve as described in claim 2, characterized in that the valve chamber has, on its outside, a catch recess and in that the rotating piece has, concentric to the valve plug a cylindrical projection with at least one detent which engages the catch recess.

10. The regulating valve as described in claim 1, characterized in that the annular disk has a cylindrical projection which has, on its face, opposing recesses which overlap the connecting pieces of the housing.

11. The regulating valve as described in claim 10, characterized by the provision on the outside of the valve chamber of a rotation limiting stop cooperating with a rotation limiting stop on the rotating piece.

12. The regulating valve as described in claim 11, characterized in that the valve chamber has, on its outside, a catch recess and in that the rotating piece has, concentric to the valve plug a cylindrical projection with at least one detent which engages the catch recess.

13. The regulating valve as described in claim 10, characterized in that the valve chamber has, on its outside, a catch recess and in that the rotating piece has, concentric to the valve plug a cylindrical projection with at least one detent which engages the catch recess.

14. The regulating valve as described in claim 1, characterized by the provision on the outside of the valve chamber of a rotation limiting stop cooperating with a rotation limiting stop on the rotating piece.

15. The regulating valve as described in claim 14, charcterized in that the valve chamber has, on its outside, a catch recess and in that the rotating piece has, concentric to the valve plug a cylindrical projection with at least one detent which engages the catch recess.

16. The regulating valve as described in claim 1, characterized in that the valve chamber has, on its outside, a catch recess and in that the rotating piece has, concentric to the valve plug a cylindrical projection with at least one detent which engages the catch recess.

17. The regulating valve as described in claim 1, characterized in that the longitudinal axes of the connecting pieces are, in relation to the axis of rotation of the regulating valve, axially offset from one another.

18. Regulating valve as described in claim 1, characterized in that the valve plug has, on its outer periphery, two grooves, one of which is assigned to the inlet connecting piece and the other to the outlet connecting piece, the at least one groove being connected to each other in terms of flow by an axial channel.

19. Regulating valve as described in claim 1, characterized in that the interior of the valve chamber has a step after which a sealing engagement takes place between the valve chamber and the valve plug.

20. Regulating valve as described in claim 1, characterized in that the annular disc, the valve chamber and the connecting pieces are designed as an insert part which can be inserted into the housing.

21. Regulating valve as described in claim 20, characterized by the provision at the upper outer edge of the housing of a rotating stop and of a counter-stop at the base of the rotating piece.

22. Regulating valve as described in claim 21, characterized in that the insert with detents can be locked in the openings of the housing.

23. Regulating valve as described in claim 22, characterized in that the rotating piece with integrated valve plug can be locked on the valve chamber by means of at least one detent projection.

* * * * *